(12) United States Patent
Chen et al.

(10) Patent No.: US 11,597,722 B2
(45) Date of Patent: Mar. 7, 2023

(54) CRYSTAL FORM D OF PYRAZINE-2(1H)-KETONE COMPOUND AND PREPARATION METHOD THEREFOR

(71) Applicant: ZHANGZHOU PIEN TZE HUANG PHARMACEUTICAL CO., LTD., Fujian (CN)

(72) Inventors: Zhiliang Chen, Zhangzhou (CN); Zhiyi Luo, Zhangzhou (CN); Yichao Zhuang, Zhangzhou (CN); Jinxia Lin, Zhangzhou (CN); Longhui Gao, Zhangzhou (CN); Zhifei Fu, Shanghai (CN); Miaorong Luo, Shanghai (CN); Yang Zhang, Shanghai (CN); Jian Li, Shanghai (CN); Shuhui Chen, Shanghai (CN)

(73) Assignee: ZHANGZHOU PIEN TZE HUANG PHARMACEUTICAL CO., LTD., Fujian (CN)

( * ) Notice: Subject to any disclaimer, the term of this patent is extended or adjusted under 35 U.S.C. 154(b) by 0 days.

(21) Appl. No.: 17/633,299

(22) PCT Filed: Aug. 4, 2020

(86) PCT No.: PCT/CN2020/106901
§ 371 (c)(1),
(2) Date: Feb. 7, 2022

(87) PCT Pub. No.: WO2021/023195
PCT Pub. Date: Feb. 11, 2021

(65) Prior Publication Data
US 2022/0281853 A1    Sep. 8, 2022

(30) Foreign Application Priority Data

Aug. 8, 2019  (CN) .......................... 201910731106.1
Nov. 1, 2019  (CN) .......................... 201911059942.6

(51) Int. Cl.
C07D 403/14    (2006.01)
(52) U.S. Cl.
CPC ........ C07D 403/14 (2013.01); C07B 2200/13 (2013.01)
(58) Field of Classification Search
CPC .................................................. C07D 403/14
See application file for complete search history.

(56) References Cited

U.S. PATENT DOCUMENTS

| 2006/0293339 A1 | 12/2006 | Chakravarty et al. |
| 2014/0088100 A1 | 3/2014 | Bifulco, Jr. et al. |
| 2016/0244449 A1 | 8/2016 | Lu et al. |
| 2017/0260168 A1 | 9/2017 | Andrews et al. |
| 2021/0040070 A1 | 2/2021 | Zhang et al. |

FOREIGN PATENT DOCUMENTS

| CN | 101468965 A | 7/2009 |
| CN | 104540809 A | 4/2015 |
| CN | 107438607 A | 12/2017 |
| WO | WO-2017070708 A1 | 4/2017 |
| WO | WO-2019154364 A1 | 8/2019 |

OTHER PUBLICATIONS

Nov. 6, 2020 International Search Report issued in International Patent Application No. PCT/CN2020/106901.
Nov. 6, 2020 Written Opinion of the International Searching Authority issued in International Patent Application No. PCT/CN2020/106901.
Priority document—Chinese Patent Application CN2019107311061 (not published).
Priority document—Chinese Patent Application CN2019110599426 (not published).
Aug. 9, 2022 Japanese First Office Action issued in Japanese Patent Application No. 2022507756.
Aug. 9, 2022 Japanese First Office Action issued in Japanese Patent Application No. 2022507756 EN Version.
Sep. 14, 2022 Extended European Search Report issued in International Patent Application No. PCT/CN2020/106901.

*Primary Examiner* — Samira J Jean-Louis
(74) *Attorney, Agent, or Firm* — Harness, Dickey & Pierce, P.L.C.

(57) ABSTRACT

The present invention disclosed a crystal form of pyrazine-2(1H)-ketone compound and a preparation method therefor. Specifically disclosed is a method for preparing a compound of formula (II) and a crystal form thereof.

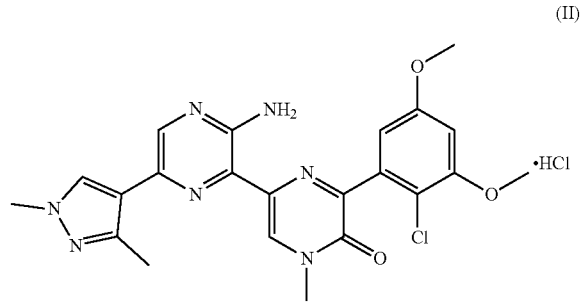

9 Claims, 2 Drawing Sheets

CRYSTAL FORM D OF PYRAZINE-2(1H)-KETONE COMPOUND AND PREPARATION METHOD THEREFOR

CROSS-REFERENCE TO RELATED APPLICATIONS

This application is a U.S. National Phase Application under 35 U.S.C. 371 of International Application No. PCT/CN2020/106901, filed on Aug. 4, 2020, which claims the benefit of Chinese Patent Application No. 201910731106.1, filed on Aug. 8, 2019, and Chinese Patent Application No. 201911059942.6, filed on Nov. 1, 2019. The entire disclosures of the above applications are incorporated herein by reference.

TECHNICAL FIELD

The present disclosure relates to a crystal form of pyrazine-2(1H)-ketone compound and preparation method therefor, specifically disclosed is a method for preparing a compound of formula (II) and a crystal form thereof.

BACKGROUND

Fibroblast growth factor receptor (FGFR) is a receptor for fibroblast growth factor (FGF) signaling, which is a family consisting of four members (FGFR1, FGFR2, FGFR3, FGFR4) and a glycoprotein composed of extracellular immunoglobulin (Ig)-like domains, hydrophobic transmembrane domains and intracellular parts including tyrosine kinase domains. Fibroblast growth factor (FGF) plays an important role in many physiological regulation processes such as cell proliferation, cell differentiation, cell migration and angiogenesis through these receptors (FGFR). There are many evidences show that the abnormality of FGF signaling pathway (high expression, gene amplification, gene mutation, chromosome reorganization, etc.) is directly related to many pathological processes such as tumor cell proliferation, migration, invasion and angiogenesis. Therefore, FGFR has become an important therapeutic target, attracting extensive research and development interest.

Content of the Present Invention

The present disclosure provides a crystal form C of compound of formula (II), the X-ray powder diffraction pattern thereof has characteristic diffraction peaks at the following 2θ angles: 9.42±0.20°, 26.28±0.20°, and 27.72±0.20°.

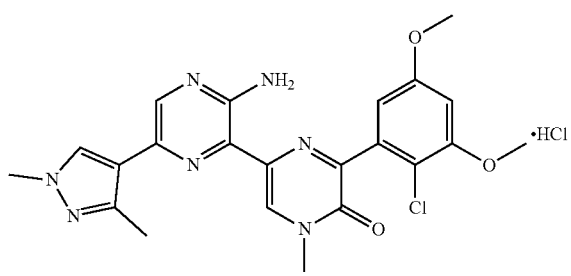

(II)

In some embodiments of the present disclosure, the X-ray powder diffraction pattern of the crystal form C of compound of formula (II) has characteristic diffraction peaks at the following 2θ angles: 9.42±0.20°, 10.92±0.20°, 14.60±0.20°, 20.08±0.20°, 23.19±0.20°, 24.11±0.20°, 26.28±0.20°, and 27.72±0.20°.

In some embodiments of the present disclosure, the X-ray powder diffraction pattern of the crystal form C of compound of formula (II) has characteristic diffraction peaks at the following 2θ angles: 9.42±0.20°, 10.92±0.20°, 14.60±0.20°, 19.31±0.20°, 20.08±0.20°, 23.19±0.20°, 24.11±0.20°, 24.92±0.20°, 26.28±0.20°, 27.08±0.20°, 27.72±0.20°, and 29.29±0.20°.

In some embodiments of the present disclosure, the X-ray powder diffraction pattern of the crystal form C of compound of formula (II) has characteristic diffraction peaks at the following 2θ angles: 9.42°, 10.92°, 14.60°, 16.61°, 19.31°, 20.08°, 23.19°, 24.11°, 24.92°, 26.28°, 27.08°, 27.72°, 29.29°, 30.39°, 33.92°, and 38.33°.

In some embodiments of the present disclosure, the XRPD pattern of the crystal form C of compound of formula (II) is as shown in FIG. 1.

In some embodiments of the present disclosure, the analytical data of the XRPD pattern of the crystal form C of compound of formula (II) is as shown in Table 1.

TABLE 1

Analytical data of the XRPD pattern of the crystal form D of compound of formula (II)

| No. | 2θ Angle (°) | d-spacing (Å) | Intensity | Relative intensity (%) |
|---|---|---|---|---|
| 1 | 9.42 | 9.39 | 562.76 | 80.09 |
| 2 | 10.92 | 8.10 | 301.58 | 42.92 |
| 3 | 14.60 | 6.07 | 366.95 | 52.22 |
| 4 | 16.61 | 5.34 | 72.51 | 10.32 |
| 5 | 19.31 | 4.60 | 159.94 | 22.76 |
| 6 | 20.08 | 4.42 | 182.15 | 25.92 |
| 7 | 23.19 | 3.84 | 193.08 | 27.48 |
| 8 | 24.11 | 3.69 | 163.29 | 23.24 |
| 9 | 24.92 | 3.57 | 179.29 | 25.51 |
| 10 | 26.28 | 3.39 | 467.91 | 66.59 |
| 11 | 27.08 | 3.29 | 158.73 | 22.59 |
| 12 | 27.72 | 3.22 | 702.70 | 100.00 |
| 13 | 29.29 | 3.05 | 143.32 | 20.40 |
| 14 | 30.39 | 2.94 | 87.06 | 12.39 |
| 15 | 33.92 | 2.64 | 41.82 | 5.95 |
| 16 | 38.33 | 2.35 | 84.58 | 12.04 |

In some embodiments of the present disclosure, the differential scanning calorimetry curve of the crystal form C of the compound of formula (II) has an endothermic peak with an onset at 179.1° C.±2.0° C., and an endothermic peak with an onset at 247.1° C.±2.0° C.

In some embodiments of the present disclosure, the DSC spectrum of the crystal form C of compound of formula (II) is as shown in FIG. 2.

In some embodiments of the present disclosure, the thermogravimetric analysis curve of the crystal form C of the compound of formula (II) shows a weight loss of 7.11% at 190.0° C. 3.0° C., a weight loss of 12.10% at 250.0° C.±3.0° C., and a weight loss of 14.12% at 290.0° C. 3.0° C.

In some embodiments of the present disclosure, the TGA spectrum of the crystal form C of compound of formula (II) is as shown in FIG. 3.

The present disclosure also provides a use of the crystal form C of the compound of formula (II) in the manufacture of a medicament for treating a disease related to FGFR.

Technical Effects

The crystal form C of compound of formula (II) has good stability and is easy to be formulated. According to the experimental examples of trifluoroacetate of compound of formula (I), it can be seen that the crystal form C of compound of formula (II) has a good inhibitory activity against wild-type FGFR, and relative high selectivity towards FGFR2 and FGFR3 compared to FGFR1 and FGFR4. The pharmacokinetic indexes of the crystal form C of compound of formula (II) in mouse are good.

The trifluoroacetate of compound of formula (I) has a good inhibitory activity against wild-type FGFR, and relative high selectivity towards FGFR2 and FGFR3 compared to FGFR1 and FGFR4. The pharmacokinetic indexes of the trifluoroacetate of compound of formula (I) in mouse are good.

Definition and Description

Unless otherwise stated, the following terms and phrases used herein are intended to have the following meanings. A specific term or phrase should not be considered uncertain or unclear unless specifically defined, but should be understood in its ordinary meaning. When a trade name appears herein, it is intended to refer to the corresponding commodity or an active ingredient thereof.

The compounds of the present disclosure can be prepared by various synthetic methods well known to a person skilled in the art, including the specific embodiments listed below, the embodiments formed by the combination with other chemical synthesis methods, and equivalent alternative embodiments well known to a person skilled in the art, wherein the preferred embodiments include but are not limited to the examples of the present disclosure.

The chemical reactions of the embodiments of the present disclosure are carried out in a suitable solvent, and the solvent should be suitable for the chemical change, and the reagents and materials required therefor of the present disclosure. In order to obtain the compounds of the present disclosure, it is sometimes necessary for those skilled in the art to modify or select the synthetic steps or reaction schemes based on the existing embodiments.

The present disclosure will be specifically described below by way of embodiments, but the scope of the present disclosure is not limited thereto.

All solvents used in the present disclosure are commercially available and can be directly used without further purification.

The present invention uses the following abbreviations: aq stands for water; HATU stands for O-(7-azabenzotriazol-1-yl)-N,N,N',N'-tetramethyluronium hexafluorophosphate; EDC stands for N-(3-dimethylaminopropyl)-N'-ethylcarbodiimide hydrochloride; m-CPBA stands for 3-chloroperbenzoic acid; eq stands for equivalent, equivalent; CDI stands for N,N'-carbonyldiimidazole; DCM stands for dichloromethane; PE for petroleum ether; DIAD for diisopropyl azodicarboxylate; DMF for N,N-dimethylformamide; DMSO for dimethyl sulfoxide; EtOAc for ethyl acetate; EtOH for ethanol; MeOH for methanol; CBz stands for benzyloxycarbonyl, which is an amine protecting group; BOC stands for tert-butoxycarbonyl, which is an amine protecting group; HOAc stands for acetic acid; NaCNBH3 stands for sodium cyanoborohydride; r.t. stands for room temperature; 0/N stands for overnight; THF stands for tetrahydrofuran; Boc2O for di-tert-butyl dicarbonate; TFA for trifluoroacetic acid; DIPEA for ethyldiisopropylamine; SOCl2 for thionyl chloride; CS2 for carbon disulfide; TsOH for p-toluenesulfonic acid; NFSI stands for N-fluoro-N-(benzenesulfonyl)benzenesulfonamide; NCS stands for 1-chloropyrrolidine-2,5-dione; n-Bu4NF for tetrabutylammonium fluoride; iPrOH stands for 2-propanol; mp stands for melting point; LDA stands for lithium diisopropylamide.

The solvents used in the present disclosure are commercially available, and the commercially available compound adopts the supplier's catalog name. When the mixed solvent is added to the reaction solution, the solvents can be mixed first and then added to the reaction solution; or each single solvent can be added to the reaction solution in sequence and mixed in the reaction system.

Compounds are named according to conventional naming principles in the field or using ChemDraw® software, and commercially available compounds are named using supplier catalog names.

X-Ray Powder Diffraction Analysis (X-Ray Powder Diffractometer, XRPD) in the Present Disclosure About 10 to 20 mg of the sample was subjected to XRPD detection.

Detailed XRPD parameters are as follows:

X-ray tube: Cu, k2, ($\lambda$=1.54056 Å).

X-ray tube voltage: 40 kV, X-ray tube current: 40 mA

Divergence slit: 0.60 mm

Detector slit: 10.50 mm

Anti-scattering slit: 7.10 mm

Scanning range: 4-40 deg

Step size: 0.02 deg

Step time: 0.12 second

Rotation speed of sample tray: 15 rpm

Differential Scanning Calorimetry Analysis (Differential Scanning Calorimeter, DSC) in the Present Disclosure The sample (0.5-1 mg) was weighed and placed in a DSC aluminum crucible for analysis, and the sample was then heated from 25° C. to 300° C. or 350° C. with a heating rate of 10° C./min.

Thermogravimetric analysis (Thermal Gravimetric Analyzer, TGA) in the present disclosure The sample (2-5 mg) was weighed and placed in a TGA platinum crucible for analysis, and the sample was heated under the condition of 25 mL/min $N_2$ with a heating rate of 10° C./min from room temperature to 300° C. or until a weight loss reached 20%.

DETAILED DESCRIPTION OF THE PREFERRED EMBODIMENT

Figure 1:
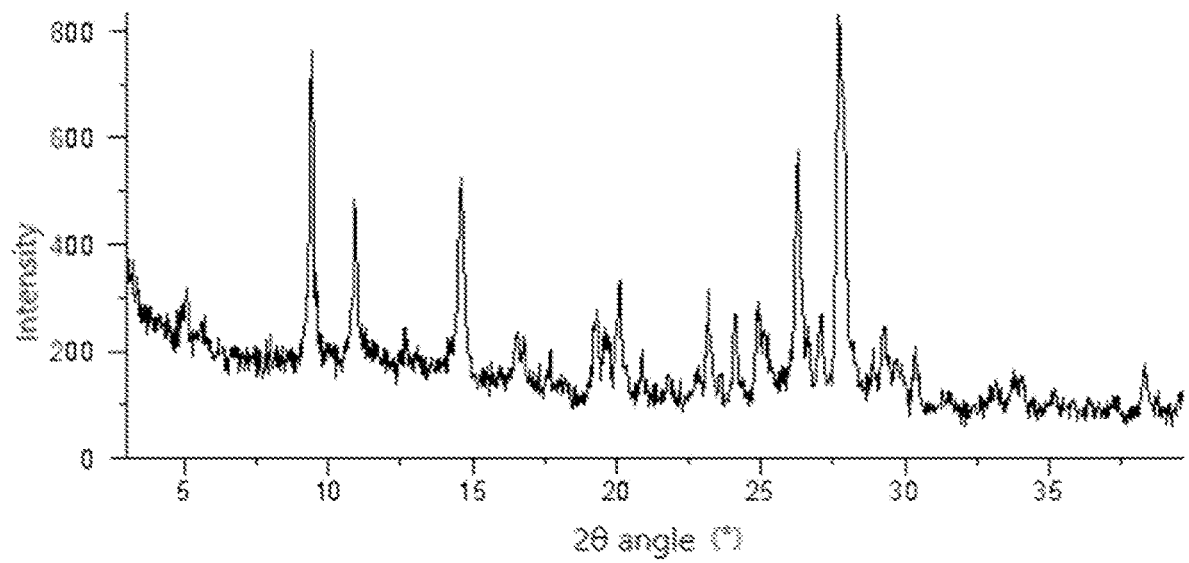
FIG. 1 is the XRPD pattern of the crystal form C of compound of formula (II) measured by Cu-K$\alpha$ radiation.

The present disclosure will be specifically described below by way of embodiments carried out, but the scope of the present disclosure is not limited thereto. The present invention has been described in detail herein, wherein specific embodiments thereof are also disclosed, for those skilled in the art, it is obvious that various changes and improvements can be made to the specific embodiments of the present invention without departing from the spirit and scope of the present invention.

Example 1: Preparation and Synthesis of the Compound of Formula (I) and the Trifluoroacetate Thereof

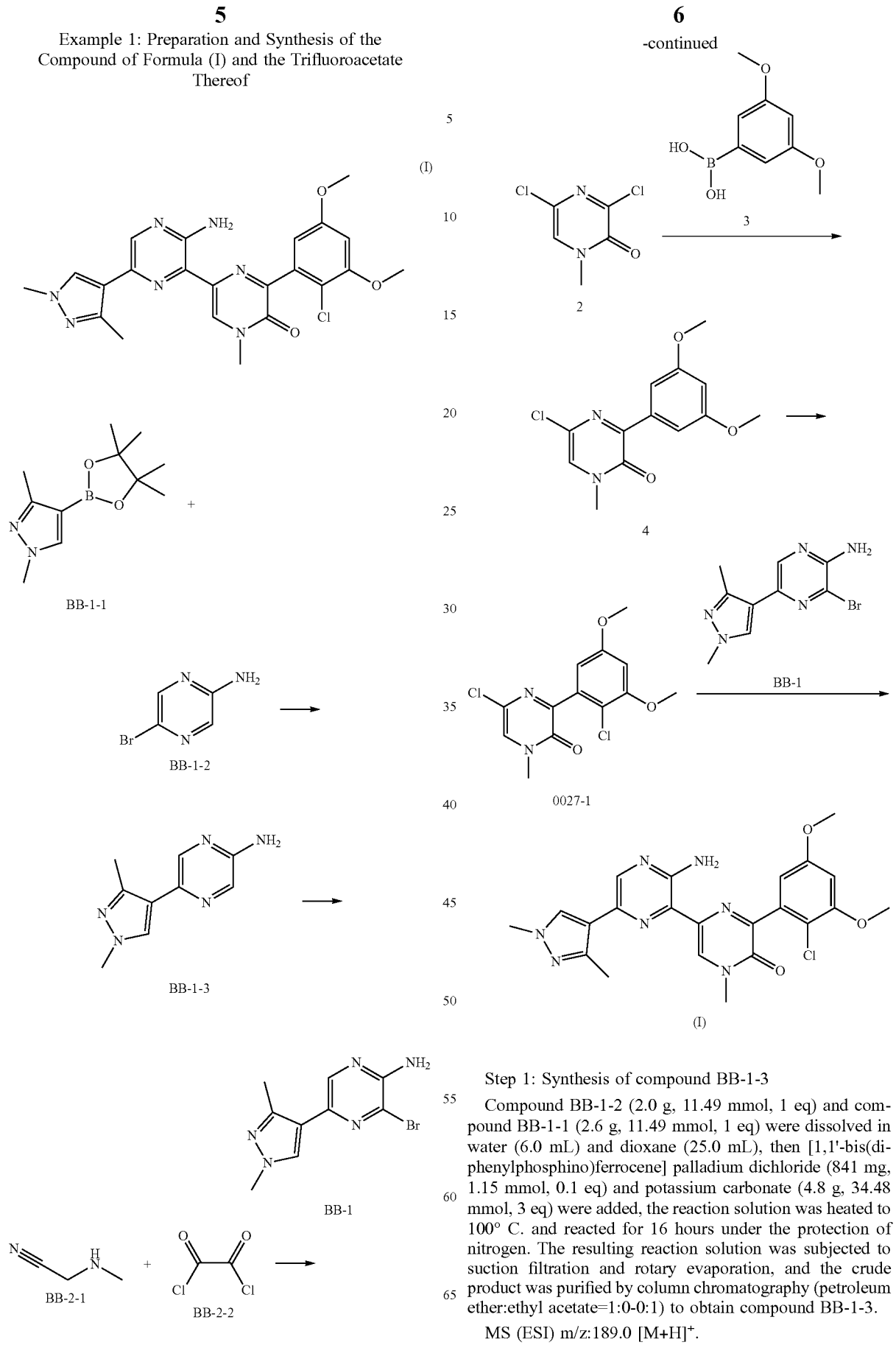

Step 1: Synthesis of compound BB-1-3

Compound BB-1-2 (2.0 g, 11.49 mmol, 1 eq) and compound BB-1-1 (2.6 g, 11.49 mmol, 1 eq) were dissolved in water (6.0 mL) and dioxane (25.0 mL), then [1,1'-bis(diphenylphosphino)ferrocene] palladium dichloride (841 mg, 1.15 mmol, 0.1 eq) and potassium carbonate (4.8 g, 34.48 mmol, 3 eq) were added, the reaction solution was heated to 100° C. and reacted for 16 hours under the protection of nitrogen. The resulting reaction solution was subjected to suction filtration and rotary evaporation, and the crude product was purified by column chromatography (petroleum ether:ethyl acetate=1:0-0:1) to obtain compound BB-1-3.

MS (ESI) m/z:189.0 [M+H]+.

Step 2: Synthesis of Compound BB-1

Compound BB-1-3 (0.5 g, 2.64 mmol, 1 eq) and pyridine (209 mg, 2.64 mmol, 213.28 μL, 1 eq) were added to chloroform (20.0 mL), cooled to 0° C. and then bromine (422 mg, 2.64 mmol, 136.22 μL, 1 eq) was added. The reaction solution was reacted for 18 hours at room temperature of 28° C. The reaction was quenched with sodium thiosulfate (1.0 mL), then subjected to suction filtration, the filtrate was concentrated. The crude product was purified by flash silica gel column chromatography (petroleum ether: ethyl acetate=1:0-1:1) to obtain Compound BB-1. MS (ESI) m/z: 267.9 [M+H]$^+$.

$^1$H NMR (400 MHz, MeOH) δ: 8.12 (s, 1H) 7.90 (s, 1H) 3.86 (s, 3H) 2.43 (s, 3H).

Step 3: Synthesis of compound 2

Under the protection of nitrogen, compound BB-2-1 (2.0 g, 18.77 mmol, 2.17 mL, 1 eq, HCl) was dissolved in chlorobenzene (15.0 mL), and compound BB-2-2 (8.3 g, 65.69 mmol, 5.8 mL, 3.5 eq) was added dropwise at 25° C., the mixture was slowly heated to 90° C. and stirred for 16 hours. Water (30.0 mL) and ethyl acetate (30.0 mL) were added to the reaction system, and allowed to stand still for layer separation. At the same time, the aqueous phase was extracted three times with ethyl acetate (20.0 mL, 20.0 mL, 20.0 mL). The organic phases were combined, washed once with saturated sodium chloride solution (30.0 mL), and finally dried with anhydrous sodium sulfate, filtered and concentrated under reduced pressure. The crude product was separated and purified by column chromatography (petroleum ether:ethyl acetate=1:0-2:1) to obtain compound 2. MS (ESI) m/z: 178.7 [M+1]

$^1$H NMR (400 MHz, CHCl$_3$) δ:7.26 (s, 1H), 3.61 (s, 3H).

Step 4: Synthesis of compound 4

In a microwave tube, under the protection of nitrogen, compound 2 (0.2 g, 1.12 mmol, 1 eq) and compound 3 (213 mg, 1.17 mmol, 1.05 eq) were dissolved in the mixed solution of dioxane (1.5 mL) and water (1.5 mL), palladium tetrakistriphenylphosphorus (65 mg, 55.86 μmol, 0.05 eq) and sodium carbonate (130 mg, 1.23 mmol, 1.1 eq) were added, and the mixture was stirred in microwave at 120° C. for 30 minutes. The reaction solution was concentrated directly. The crude product was separated by column chromatography (petroleum ether:ethyl acetate=1:0-0:1) (TLC detection, petroleum ether:ethyl acetate=1:1) to obtain compound 4. MS (ESI) m/z: 279.0 [M+1]

$^1$1-1NMR (400 MHz, CHCl$_3$) δ:7.64 (d, 2H), 7.28 (s, 1H), 6.59 (t, 1H), 3.86 (s, 6H), 3.61 (s, 3H).

Step 5: Synthesis of compound 0027-1

Under the protection of nitrogen, compound 4 (250 mg, 890.61 μmol, 1 eq) was dissolved in a mixed solvent of acetonitrile (20.0 mL) and dichloromethane (5.0 mL), and then sulfonyl chloride (84 mg, 623.43 μmol, 62.33 μL, 0.7 eq) in acetonitrile (2.5 mL) was added dropwise slowly at 0° C. The mixture was stirred at 0° C. for 10 minutes. The reaction was quenched by adding methanol (5.0 mL) to the reaction solution, and the reaction solution was concentrated to dryness under reduced pressure. The crude product was separated by column chromatography (petroleum ether:ethyl acetate=1:0-0:1) (TLC detection, petroleum ether:ethyl acetate=1:1) to obtain compound 0027-1. MS (ESI) m/z: 314.9 [M+H]$^+$.

Step 6: Synthesis of the compound of formula (I)

In a three-necked flask, compound 0027-1 (59 mg, 186.49 μmol, 1 eq), bis(pinacolato)diboron (52 mg, 205.14 μmol, 1.1 eq), and palladium acetate (5 mg, 20.51 μmol, 0.11 eq) and 2-dicyclohexylphosphorus-2,4,6-triisopropylbiphenyl (20 mg, 41.03 μmol, 0.22 eq), potassium acetate (60 mg, 615.42 μmol, 3.3 eq) were added to dioxane (4.0 mL) solution. The air in the reaction system was replaced with nitrogen, and under the saturation of nitrogen, the reaction solution was heated up to 100° C., refluxed and stirred for 30 minutes, then cooled to 25° C. Compound BB-1 (50 mg, 186.49 μmol, 1 eq), dichloromethane complex of [1,1'-bis(diphenylphosphino)ferrocene] palladium dichloride (15 mg, 18.65 μmol, 0.1 eq), potassium carbonate (77 mg, 559.47 μmol, 3 eq), dioxane (4.0 mL) and water (2.0 mL) were added. The air in the reaction system was replaced with nitrogen, and under the saturation of nitrogen, the reaction solution was heated to 100° C. and refluxed for 8 hours with stirring. The reaction solution was concentrated directly. The crude product obtained was separated and purified by high performance liquid chromatography (column: Boston Green ODS150×30 mm 5 μm; mobile phase: [water (0.1% TFA)-ACN]; B %: 30%-60%, 8 min) to obtain the trifluoroacetate of the compound of formula (I). MS (ESI) m/z: 468.2 [M+H]$^+$. $^1$H NMR (400 MHz, MeOH) δ: 8.79 (s, 1H), 8.09 (m, 2H), 6.76 (m, 2H), 3.93 (s, 3H), 3.89 (s, 3H), 3.84 (s, 3H), 3.80 (s, 3H), 2.54 (s, 3H). The salt was dissolved in dichloromethane, washed with saturated sodium carbonate, the organic phase is dried with anhydrous sodium sulfate, filtered, and the filtrate was spin-dried to obtain the compound of formula (I). $^1$H NMR (400 MHz, CDCl$_3$) δ: 8.51 (s, 1H), 8.15 (s, 1H), 6.71 (d, J=2.8 Hz, 1H), 6.63 (d, J=2.8 Hz, 1H), 6.43 (brs, 2H), 3.94 (s, 3H), 3.92 (s, 3H), 3.84 (s, 3H), 3.79 (s, 3H), 2.55 (s, 3H).

Example 2: Preparation of the Compound of Formula (II)

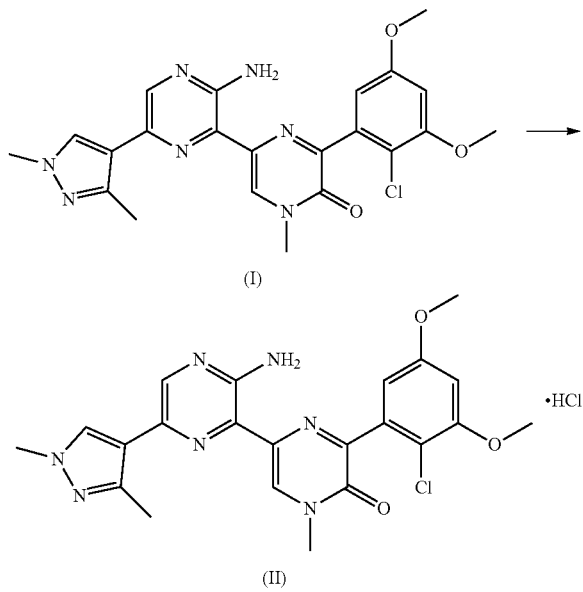

The compound of formula (I) (44.4 g, 94.89 mmol, 1 eq) was dissolved in tetrahydrofuran (450 mL), and then an ethyl acetate solution of hydrogen chloride (4 M, 94.89 mL, 4 eq) was added dropwise, and the reaction solution was stirred at 25° C. for 3 hours. The reaction liquid was filtered to obtain a yellow solid, which was dried by an oil pumpto obtain the compound of formula (II).

$^1$H NMR (400 MHz, DMSO) δ: 8.71 (s, 1H), 8.18 (s, 2H), 6.82 (d, J=2.8 Hz, 1H), 6.75 (d, J=2.8 Hz, 1H) 3.91 (s, 3H), 3.81 (s, 3H), 3.80 (s, 3H), 3.71 (s, 3H), 2.44 (s, 3H).

Example 3: Preparation of the Crystal Form C of the Compound of Formula (II)

Compound of formula (II) (0.4 g, 793.07 umol, 1 eq) was added to acetonitrile (6 mL), and the reaction solution was stirred at 50° C. for 60 hours, followed by filtration. The filter cake was dried in a vacuum drying oven at 50° C. for 3.5 hours to obtain the crystal form C of the compound of formula (II).

Experimental Example 1: Evaluation of Inhibitory Activity of Wild-Type Kinase In Vitro The $IC_{50}$ value was determined using $^{33}$P isotope-labeled kinase activity test (Reaction Biology Corp) to evaluate the inhibitory ability of the compounds to be tested on human FGFR4 and VEGFR2.

Buffer conditions: 20 mM 4-(2-hydroxyethyl)-1-piperazineethanesulfonic acid (Hepes) (pH 7.5), 10 mM $MgCl_2$, 1 mM ethylene glycol-bis-(2-aminoethyl ether) acetic acid (EGTA), 0.02% polyoxyethylene lauryl ether (Brij35), 0.02 mg/ml bovine serum albumin (BSA), 0.1 mM sodium vanadate ($Na_3VO_4$), 2 mM dithiothreitol (DTT), 1% DMSO.

Experimental steps: At room temperature, the compounds to be tested were dissolved in DMSO to prepare a 10 mM solution for use. The substrate was dissolved in the newly-prepared buffer, and the kinase to be tested was added thereto and mixed well. The DMSO solution in which the compounds to be tested were dissolved was added to the above-mentioned homogeneous reaction solution using acoustic technology (Echo 550). The compound concentration in the reaction solution is 10 μM, 3.33 μM, 1.11 μM, 0.370 μM, 0.123 μM, 41.2 nM, 13.7 nM, 4.57 nM, 1.52 nM, 0.508 nM, or 10 μM, 2.50 μM, 0.62 μM, 0.156 μM, 39.1 nM, 9.8 nM, 2.4 nM, 0.61 nM, 0.15 nM, 0.038 nM. After incubating for 15 minutes, to the reaction solution was added $^{33}$P—ATP (activity: 0.01 μCi/μL, with corresponding concentration listed in Table 1) to start the reaction. The supplier product number, batch number, and concentration information in the reaction solution of FGFR1, FGFR4 and substrate thereof are listed in Table 2. After the reaction was carried out at room temperature for 120 minutes, the reaction solution was spotted on P81 ion exchange filter paper (Whatman #3698-915). After the filter paper was repeatedly washed with 0.75% phosphoric acid solution, the radioactivity of the phosphorylated substrate remaining on the filter paper was measured. The kinase activity data was expressed by comparing the kinase activity of the groups containing the compounds to be tested with that of the blank group (containing only DMSO). The $IC_{50}$ value was obtained by curve fitting using Prism4 software (GraphPad), and the experimental results were shown in Table 3.

TABLE 2

Related information about kinases, substrates and ATP in in-vitro tests.

| Kinase | Supplier | Cat# | Lot # | ATP concentration (μM) |
|---|---|---|---|---|
| FGFR1 | Invitrogen | PV3146 | 28427Q | 5 |
| FGFR2 | Invitrogen | PV3368 | 31517I | 5 |
| FGFR3 | Invitrogen | PV3145 | 28459R | 30 |
| FGFR4 | Invitrogen | P3054 | 26967J | 2.5 |

| Substrate | Supplier | Cat# | Lot # | Substrate concentration in reaction solution (μM) |
|---|---|---|---|---|
| pEY (mg/ml) + Mn | Sigma | P7244-250MG | 062K5104V | 0.2 |
| pEY (mg/ml) + Mn | Sigma | P7244-250MG | 062K5104V | 0.2 |
| pEY (mg/ml) + Mn | Sigma | P7244-250MG | 062K5104V | 0.2 |
| pEY (mg/ml) + Mn | Sigma | P7244-250MG | 062K5104V | 0.2 |

TABLE 3

In vitro screening test results of the compounds of the present invention

| Compound | IC$_{50}$(nM) | | | | Selectivity | |
|---|---|---|---|---|---|---|
| | FGFR1 | FGFR2 | FGFR3 | FGFR4 | FGFR1/2 | FGFR1/3 |
| Trifluoroacetate of compound of formula (I) | 2.12 | 0.53 | 0.69 | 106 | 4.02 | 3.06 |

Conclusion: The trifluoroacetate of compound of formula (I) has a good inhibitory activity against wild-type FGFR, and relative high selectivity towards FGFR2 and FGFR3 compared to FGFR1 and FGFR4.

Experimental Example 2: Evaluation of Pharmacokinetic of Compound

Experimental purpose: To test the pharmacokinetics of the compound in mice

Experimental Materials:

CD-1 mouse (male), vehicle (0.5% (w/v) methylcellulose 0.5% (v/v) Tween 80 aqueous solution), trifluoroacetate of compound 0027.

1. Formulation of preparations for administration:

The vehicle was an aqueous solution of 0.5% (w/v) methylcellulose and 0.5% (v/v) Tween 80, and it was prepared according to the following procedure:

a. About 50% volume of purified water was added to a suitable container and heated to about 60° C. to 70° C.

b. When the water temperature reached the specified value range, the heater was turned off. The required amount of methylcellulose was added slowly to the above container with constant stirring.

c. The mixture was stirred continuously at 4° C. until a clear solution was obtained visually.

d. The required volume of Tween 80 was added to the above solution. The mixture was stirred continuously until Tween 80 became being evenly dispersed and a clear solution was obtained visually.

e. The above solution was diluted to the final volume using an appropriate amount of pure water.

f Continus stirring until a homogeneous solution was formed.

Formulation of preparations for intragastric administration:

a. An appropriate amount of the test product was weighed and put into a glass bottle;

b. 70% volume of vehicle (0.5% (w/v) methyl cellulose 0.5% (v/v) Tween 80 aqueous solution) was added;

c. The preparation was stirred until it was visually homogeneous, and subjected to ultrasound in water bath as needed;

e. Make up the remaining volume of 0.5% methylcellulose+0.5% Tween 80, and the mixture was stirred until being visually homogeneous.

2. Administration

Animals in groups 1 and 2 were administrated 5 mg/mL and 30 mg/mL compounds by single gavage, with a dose volume of 10 mL/kg.

The body weight of the animals was weighed before administration, and the administration volume was calculated based on the body weight.

3. Sample collection and processing

Whole blood samples (30 μL) were collected at the prescribed time (0.25, 0.5, 1, 2, 4, 6, 8, 24 h) through saphenous vein blood collection, and the actual blood collection time was recorded in the test record. The acceptable error of the collection time point was a time point within 1 hour of the administration ±1 minute, and the acceptable error of other time points is a theoretical time ±5%.

All blood samples were immediately transferred to labeled commercial centrifuge tubes containing K2-EDTA. After being collected, the the blood samples were centrifuged at 3200 rpm for 10 minutes at 4° C. to aspirate the supernatant plasma, which was quickly placed in dry ice, kept at −20° C. or a lower temperature for LC-MS/MS analysis. The pharmacokinetic parameters were calculated, and the experimental results are shown in Table 4.

TABLE 4

Pharmacokinetic test results

| Compound | Trifluoroacetate of compound of formula (I) | |
|---|---|---|
| Parameters\Dosage | 50 mpk | 300 mpk |
| $C_{max}$ (nM) | 14800 | 42100 |
| $T_{max}$ (hr) | 1.00 | 7.00 |
| $T_{1/2}$ (hr) | 2.46 | ND |
| $T_{last}$ (hr) | ND | 24.0 |
| $AUC_{0-last}$ (nM · hr) | 85826 | 699413 |
| $AUC_{0-inf}$ (nM · hr) | 95847 | ND |
| $MRT_{0-last}$ (h) | 4.33 | 11.1 |
| $MRT_{0-inf}$ (h) | 5.39 | ND |

ND stands for: Not determined.

Conclusion: The trifluoroacetate of the compound of formula (I) has good pharmacokinetic indexes in mice.

What is claimed is:

1. A crystal form D of compound of formula (II), wherein the crystal form D has an X-ray powder diffraction pattern having characteristic diffraction peaks at the following 2θ angles: 9.42±0.20°, 26.28±0.20°, and 27.72±0.20°.

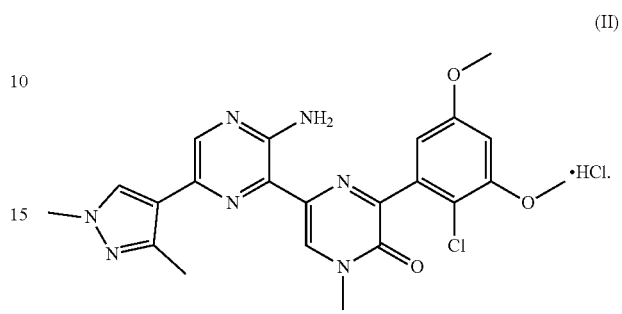

2. The crystal form D as defined in claim 1, wherein the X-ray powder diffraction pattern thereof has characteristic diffraction peaks at the following 2θ angles: 9.42±0.20°, 10.92±0.20°, 14.60±0.20°, 20.08±0.20°, 23.19±0.20°, 24.11±0.20°, 26.28±0.20°, and 27.72±0.20°.

3. The crystal form D as defined in claim 2, wherein the X-ray powder diffraction pattern thereof has characteristic diffraction peaks at the following 2θ angles: 9.42±0.20°, 10.92±0.20°, 14.60±0.20°, 19.31±0.20°, 20.08±0.20°, 23.19±0.20°, 24.11±0.20°, 24.92±0.20°, 26.28±0.20°, 27.08±0.20°, 27.72±0.20°, and 29.29±0.20°.

4. The crystal form D as defined in claim 3, wherein the X-ray powder diffraction pattern thereof has characteristic diffraction peaks at the following 2θ angles: 9.42°, 10.92°, 14.60°, 16.61°, 19.31°, 20.08°, 23.19°, 24.11°, 24.92°, 26.28°, 27.08°, 27.72°, 29.29°, 30.39°, 33.92°, and 38.33°.

5. The crystal form D as defined in claim 4, wherein the X-ray powder diffraction pattern thereof is as shown in FIG. 1.

6. The crystal form D as defined in claim 1, wherein the crystal form D has a differential scanning calorimetry curve thereof has having an endothermic peak with an onset at 179.1° C.±2.0° C., and an endothermic peak with an onset at 247.1° C.±2.0° C.

Figure 2:
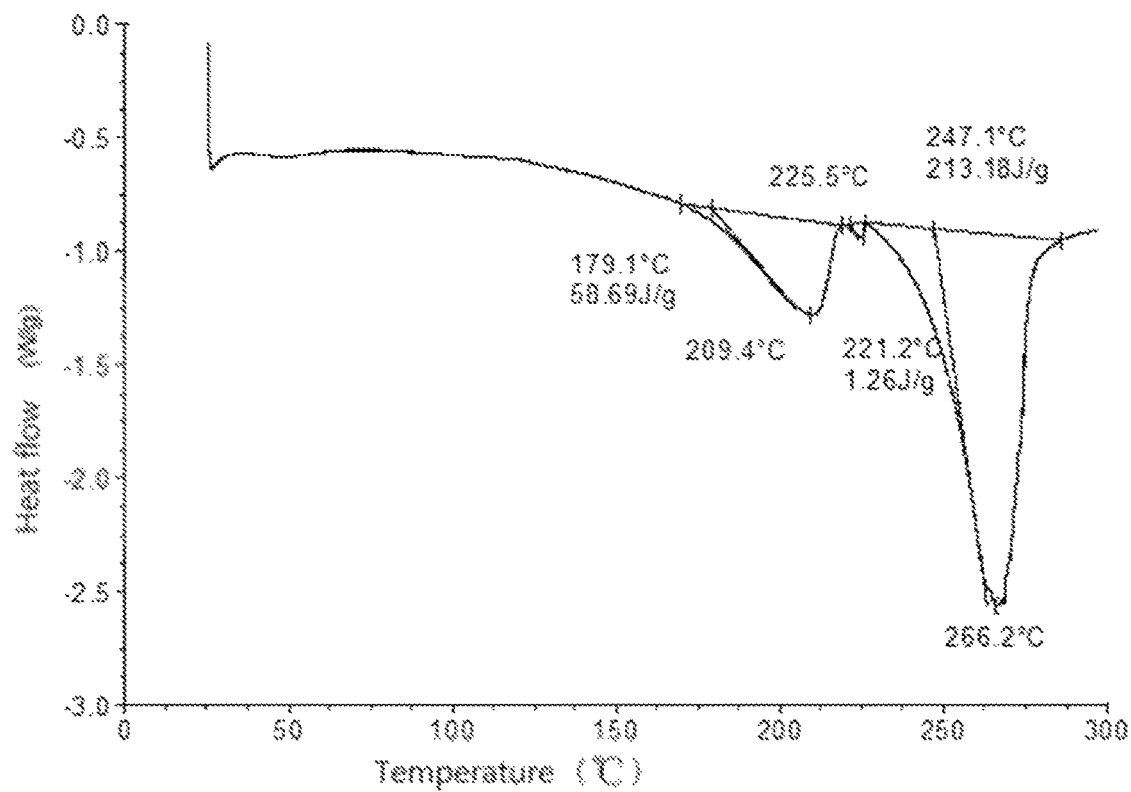
FIG. 2 is the DSC spectrum of the crystal form C of the compound of formula (II)

7. The crystal form D as defined in claim 6, wherein the DSC spectrum is as shown in FIG. 2.

8. The crystal form D as defined in claim 1, wherein the crystal form D has a thermogravimetric analysis curve showing a weight loss of 7.11% at 190.0° C.±3.0° C., a weight loss of 12.10% at 250.0° C.±3.0° C., and a weight loss of 14.12% at 290.0° C.±3.0° C.

Figure 3:
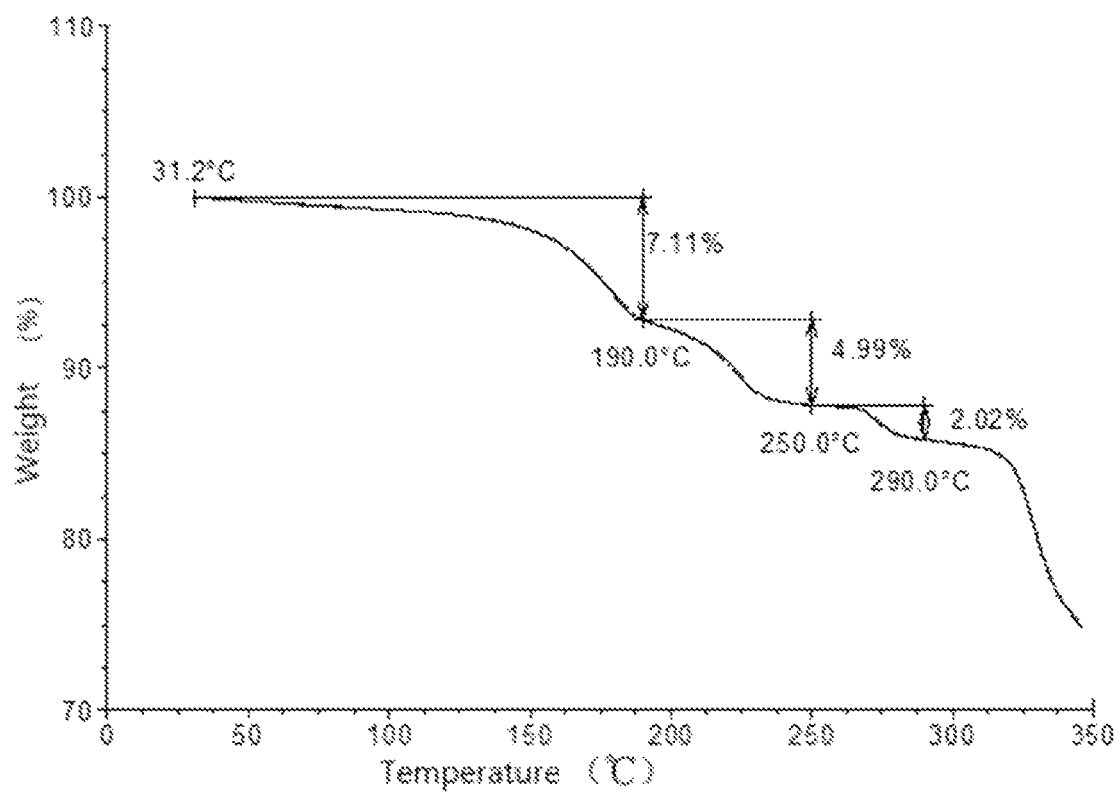
FIG. 3 is the TGA spectrum of the crystal form C of the compound of formula (II)

9. The crystal form D as defined in claim 8, wherein the TGA spectrum thereof is as shown in FIG. 3.

* * * * *